United States Patent [19]

Saville

[11] Plant 5,092

[45] Aug. 23, 1983

[54] ROSE PLANT

[75] Inventor: F. Harmon Saville, Rowley, Mass.

[73] Assignee: Nor'East Miniature Roses, Inc., Rowley, Mass.

[21] Appl. No.: 382,590

[22] Filed: May 27, 1982

[51] Int. Cl.[3] ..... A01H 5/00

[52] U.S. Cl. ..... Plt./10

[58] Field of Search ..... Plt./10

*Primary Examiner*—James R. Feyrer

*Attorney, Agent, or Firm*—Vincent G. Gioia

[57] ABSTRACT

A new miniature rose variety of clean current red coloring.

1 Drawing Figure

The present invention relates to a new and distinct variety of rose plant of the miniature rose class, which was originated by my crossing as seed parent my seedling of (Yellow Jewel × Tamango) and the rose known as "Sheri Anne" as pollen parent. The denomination of this rose is "Savathree".

Among the novel characteristics possessed by this new variety which distinguish it from its parents and all other varieties of which I am aware are well formed blooms of clean current red coloring that retain their color upon opening and aging. Asexual reproduction by budding of the new variety as performed in Essex County, Mass., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC). The terminology used in color description herein refers to plate numbers in the aforementioned color chart, e.g., "46A" is plate 46A of The Royal Horticultural Society Colour Chart.

Parentage: Seedling.

*Seed parent.*—My unpatented, unreleased seedling of (Yellow Jewel × Tamango).

*Pollen parent.*—"Sheri Anne" (U.S. Plant Pat. No. 3,826).

Class: Miniature.

The following observations are made of specimens grown under glass in Essex County, Mass. during the month of March.

FLOWER

Blooming habit: Recurrent.

A. Bud:

(1) *Size.*—Large.

(2) *Form.*—Pointed.

(3) *Color.*—After sepals fall, color of bud is current red 46A to 47A.

(4) *Sepals.*—Smooth, longer than bud with reddish tips.

(5) *Peduncle.*—Length — about ½ to 1 inch. Aspect — straight. Strength — erect. Color — near 144B.

B. Bloom:

(1) *Size.*—Average size when fully expanded — about 1½ to 1¾ inches.

(2) *Borne.*—Singly and small clusters.

(3) *Form.*—High centered at first becoming flat, petals quill to points.

(4) *Petalage.*—Number of petals under normal conditions — about 20.

(5) *Color.*—Current red (46A to 47A) buds open to clean current red colored flowers which retain coloring upon opening and aging. Petals have yellow at point of petal attachment.

C. Petals:

(1) *Texture.*—Thick.

(2) *Appearance.*—Inside and outside — satiny.

(3) *Form.*—General fan shape but with pointed apex.

(4) *Arrangement.*—Regularly arranged, shingle-like.

(5) *Petaloids in center.*—Few to none.

(6) *Persistence.*—Drop off cleanly.

(7) *Fragrance.*—Slight, sweet.

(8) *Lasting quality.*—Long lasting on plant and as cut flower.

REPRODUCTIVE ORGANS

A. Stamens, filaments and anthers:

(1) *Arrangement.*—Stamens regularly arranged around styles.

(2) *Color.*—Near 21B.

B. Pollen:

*Color.*—Near 21A.

C. Styles: Even, medium length.

D. Stigmas:

*Color.*—Near 160C.

E. Hips: None observed.

PLANT

A. Form: Spreading, compact.

B. Growth: Very vigorous, good branching from base. *Height attained.*—About 16 inches.

C. Foliage: Compound 5 to 7 leaflets.

(1) *Size.*—Medium.

(2) *Quantity.*—Abundant.

(3) *Color.*—New foliage: Upper side — near to 143A; Under side — near to 138B. Old foliage:

Upper side — near 138A; Under side — near 138B.

(4) *Shape.*—Oval.

(5) *Texture.*—Upper side is glossy and under side is matte.

(6) *Edge.*—Serrated.

(7) *Serration.*—Regular.

(8) *Leaf stem.*—Color — near to 145A. Under side — 145B.

(9) *Stipules.*—Medium, smooth.

(10) *Resistance to disease.*—Blackspot — average. Mildew — average. Rust — average.

D. Wood:

(1) *New wood.*—Color — near 144B. Bark — smooth.

(2) *Old wood.*—Color — near 146B. Bark — smooth.

E. Thorns:

(1) *Thorns.*—Quantity (main stalk) — ordinary. On laterals from stalk — normal. Form — ordinary. Length — medium. Color — Reddish green. Position — scattered.

(2) *Prickles.*—None.

F. Winter hardiness: Needs winter protection in severe climate.

I claim:

1. A new and distinct variety of rose plant of the miniature rose class, substantially as shown and described, characterized particularly by clean current red flowers which retain color upon opening and aging borne on a vigorous, spreading plant.

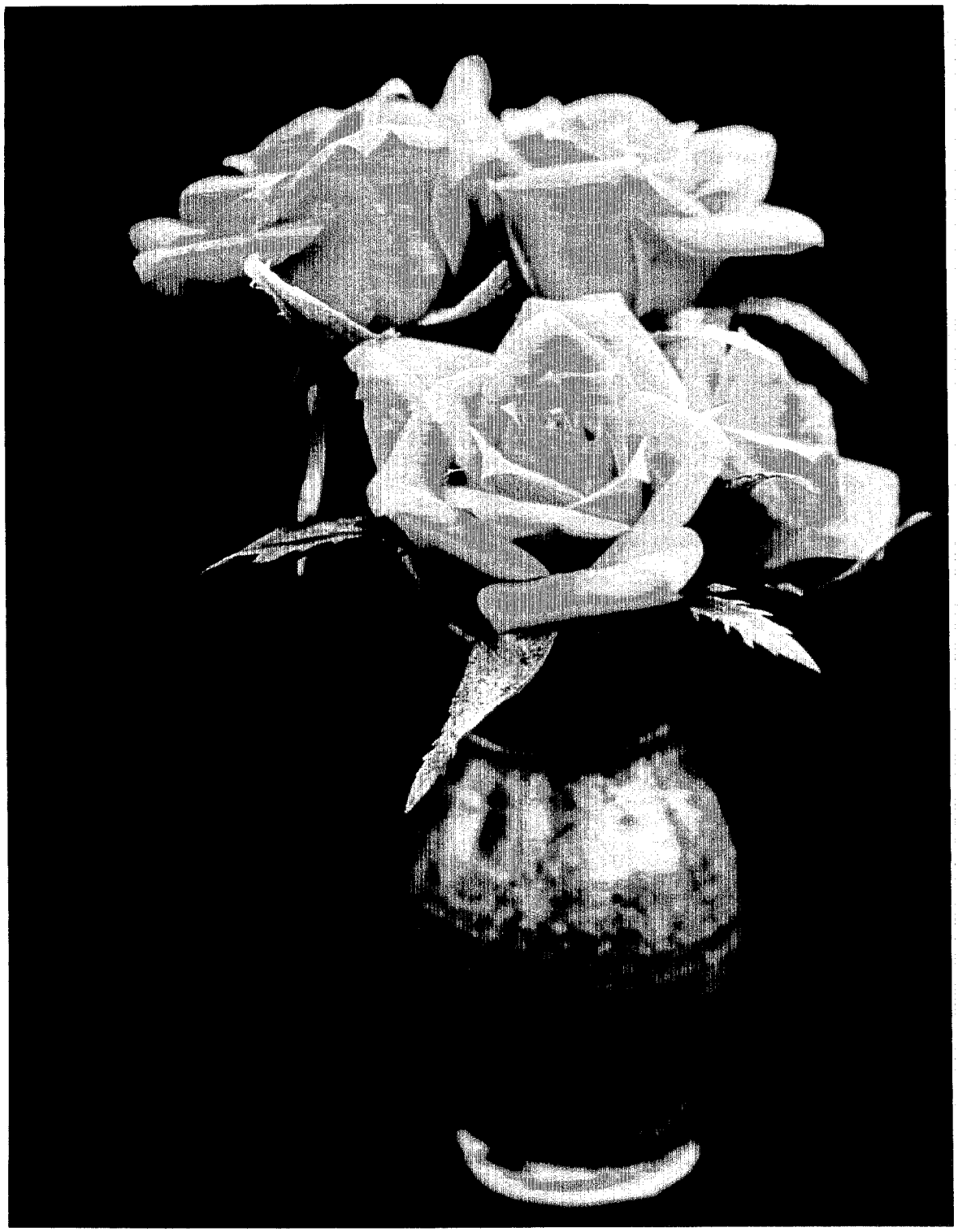

* * * * *